(12) United States Patent
Niazimbetova et al.

(10) Patent No.: US 10,041,182 B2
(45) Date of Patent: Aug. 7, 2018

(54) REACTION PRODUCTS OF AMINO ACIDS AND EPOXIES

(71) Applicant: Rohm and Haas Electronic Materials LLC, Marlborough, MA (US)

(72) Inventors: Zuhra I Niazimbetova, Westborough, MA (US); Maria Anna Rzeznik, Shrewsbury, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 15/485,454

(22) Filed: Apr. 12, 2017

(65) Prior Publication Data
US 2017/0218533 A1 Aug. 3, 2017

Related U.S. Application Data

(62) Division of application No. 14/585,228, filed on Dec. 30, 2014, now Pat. No. 9,783,905.

(51) Int. Cl.
| | | |
|---|---|---|
| *C25D 3/38* | (2006.01) | |
| *C25D 3/32* | (2006.01) | |
| *C25D 7/12* | (2006.01) | |
| *C07D 303/18* | (2006.01) | |
| *C25D 3/58* | (2006.01) | |
| *C07D 303/04* | (2006.01) | |

(52) U.S. Cl.
CPC ............ *C25D 3/38* (2013.01); *C07D 303/04* (2013.01); *C07D 303/18* (2013.01); *C25D 3/32* (2013.01); *C25D 3/58* (2013.01); *C25D 7/123* (2013.01)

(58) Field of Classification Search
CPC ... C25D 3/38; C25D 3/32; C25D 3/58; C25D 7/123; C07D 303/18; C07D 303/04
See application file for complete search history.

(56) References Cited

U.S. PATENT DOCUMENTS

| | | |
|---|---|---|
| 3,250,682 A | 5/1966 | Wilmsmann et al. |
| 3,655,534 A | 4/1972 | Kempe |
| 3,689,544 A | 9/1972 | Scanlon |
| 3,975,346 A | 8/1976 | Bosso et al. |
| 4,038,161 A | 7/1977 | Eckles et al. |
| 4,062,739 A | 12/1977 | James et al. |
| 4,081,336 A | 3/1978 | Eppensteiner et al. |
| 4,166,778 A | 9/1979 | Acimovic et al. |
| 4,169,772 A | 10/1979 | Lowery et al. |
| 4,222,829 A | 9/1980 | Popescu |
| 4,251,331 A | 2/1981 | Rosenberg |
| 4,356,277 A * | 10/1982 | Birkmeyer .............. C08G 59/52 523/406 |
| 4,447,368 A | 5/1984 | Emde et al. |
| 5,232,575 A | 8/1993 | Dodd |
| 5,684,195 A | 11/1997 | Huang et al. |
| 6,380,429 B1 | 4/2002 | Smith |
| 6,425,996 B1 | 7/2002 | Dahms et al. |
| 6,436,269 B1 | 8/2002 | Opaskar et al. |
| 6,436,306 B1 | 8/2002 | Jennings |
| 7,128,822 B2 | 10/2006 | Wang et al. |
| 7,374,652 B2 * | 5/2008 | Hayashi ................... C25D 3/38 205/125 |
| 7,662,981 B2 | 2/2010 | Wang et al. |
| 7,857,960 B2 | 12/2010 | Hayashi et al. |
| 8,012,334 B2 | 9/2011 | Reddington et al. |
| 8,048,284 B2 | 11/2011 | Reddington et al. |
| 8,262,891 B2 | 9/2012 | Wang et al. |
| 8,262,895 B2 | 9/2012 | Niazimbetova et al. |
| 8,268,157 B2 | 9/2012 | Niazimbetova |
| 8,268,158 B2 | 9/2012 | Niazimbetova et al. |
| 8,329,018 B2 | 12/2012 | Reddington et al. |
| 8,337,688 B2 | 12/2012 | Reddington et al. |
| 8,454,815 B2 | 6/2013 | Niazimbetova et al. |
| 8,747,643 B2 | 6/2014 | Niazimbetova et al. |
| 2002/0060157 A1 | 5/2002 | Calvert et al. |
| 2004/0062793 A1 | 4/2004 | Dyke |
| 2009/0139873 A1 * | 6/2009 | Wang ....................... C25D 3/38 205/298 |
| 2011/0011746 A1 | 1/2011 | Brunner et al. |
| 2011/0062029 A1 | 3/2011 | Isono et al. |
| 2011/0220514 A1 | 9/2011 | Niazimbetova |
| 2012/0292193 A1 * | 11/2012 | Roeger-Goepfert . C08G 73/028 205/118 |
| 2012/0318676 A1 * | 12/2012 | Najjar ...................... C25D 3/38 205/136 |

FOREIGN PATENT DOCUMENTS

| | | |
|---|---|---|
| EP | 0033169 A1 | 5/1981 |
| EP | 0289689 A1 | 9/1988 |
| EP | 0360744 | 3/1990 |
| EP | 1069211 A2 | 1/2001 |
| EP | 1371757 A1 | 12/2003 |
| EP | 1619274 A2 | 1/2006 |
| EP | 0174804 | 1/2007 |
| EP | 2140929 | 1/2010 |
| JP | 10102277 A | 4/1998 |
| JP | 2012255217 A | 12/2012 |
| WO | 2000043438 | 7/2000 |
| WO | 2009002385 A2 | 12/2008 |
| WO | 2009132861 A2 | 5/2009 |
| WO | 2011029781 A1 | 3/2011 |

OTHER PUBLICATIONS

Search report for corresponding European Application No. 15 19 4686 dated Sep. 5, 2016.
Search report for corresponding Taiwan Application No. 104141372 dated Sep. 10, 2016.
Search report for corresponding Taiwan Application No. 104141372 dated Jan. 20, 2017.
John E.T. Corrie, "Reaction of amino acids with exo-3, 6-epoxy-1,2,3,6-tetrahydrophthalic anhydride forms hemimaleate salts, not maleimides," ARKIVOC, May 2, 2003, pp. 69-72.
Wang, et al, "Through-hole copper electroplating using nitrotetrazolium blue chloride as a leveler", J. of Electrochemical Society, 2013, pp. D85-D88, vol. 160, No. 3.

(Continued)

*Primary Examiner* — Louis J Rufo
(74) *Attorney, Agent, or Firm* — John J. Piskorski

(57) ABSTRACT

Reaction products of one or more amino acids and one or more epoxies are included in copper and copper alloy electroplating baths to provide good throwing power. Such reaction products may plate copper and copper alloys with good surface properties and good physical reliability.

16 Claims, No Drawings

(56) References Cited

OTHER PUBLICATIONS

Dow, et al, "Microvia filling by copper electroplating using diazine black as a leveler", Electrochimica Acta, 2009, pp. 5894-5901, vol. 54.

Dow, et al, "Copper fill of microvia using a thiol-modified Cu seed layer and various levelers," J. of Electrochemical Society, 2009, pp. D314-320, vol. 156, No. 8.

Gao, et al, "Polyhydroxylalkyleneamines: a class of hydrophilic cationic polymer-based gene transfer agents," J. of Controlled Release, 2009, pp. 38-45, vol. 137.

Search report for corresponding China Application No. 201510973774.7 dated Aug. 8, 2017.

\* cited by examiner

REACTION PRODUCTS OF AMINO ACIDS AND EPOXIES

The present application is a divisional application of co-pending patent application Ser. No. 14/585,228, filed Dec. 30, 2014.

FIELD OF THE INVENTION

The present invention is directed to reaction products of amino acids and epoxies for use in copper and copper alloy electroplating baths. More specifically, the present invention is directed to reaction products of amino acids and epoxies for use in copper and copper alloy electroplating baths as levelers for providing good throwing power.

BACKGROUND OF THE INVENTION

Methods for electroplating articles with metal coatings generally involve passing a current between two electrodes in a plating solution where one of the electrodes is the article to be plated. A typical acid copper plating solution includes dissolved copper, usually copper sulfate, an acid electrolyte such as sulfuric acid in an amount sufficient to impart conductivity to the bath, a source of halide, and proprietary additives to improve the uniformity of the plating and the quality of the metal deposit. Such additives include levelers, accelerators and suppressors, among others.

Electrolytic copper plating solutions are used in a variety of industrial applications, such as decorative and anticorrosion coatings, as well as in the electronics industry, particularly for the fabrication of printed circuit boards and semiconductors. For circuit board fabrication, typically, copper is electroplated over selected portions of the surface of a printed circuit board, into blind vias and trenches and on the walls of through-holes passing between the surfaces of the circuit board base material. The exposed surfaces of blind vias, trenches and through-holes, i.e. the walls and the floor, are first made conductive, such as by electroless metallization, before copper is electroplated on surfaces of these apertures. Plated through-holes provide a conductive pathway from one board surface to the other. Vias and trenches provide conductive pathways between circuit board inner layers. For semiconductor fabrication, copper is electroplated over a surface of a wafer containing a variety of features such as vias, trenches or combinations thereof. The vias and trenches are metallized to provide conductivity between various layers of the semiconductor device.

It is well known in certain areas of plating, such as in electroplating of printed circuit boards ("PCBs"), that the use of levelers in the electroplating bath can be crucial in achieving a uniform metal deposit on a substrate surface. Electroplating a substrate having irregular topography can pose difficulties. During electroplating a voltage drop typically occurs within apertures in a surface, which can result in an uneven metal deposit between the surface and the apertures. Electroplating irregularities are exacerbated where the voltage drop is relatively extreme, that is, where the apertures are narrow and tall. Consequently, depositing a metal layer of substantially uniform thickness is frequently a challenging step in the manufacture of electronic devices. Leveling agents are often used in copper plating baths to provide substantially uniform, or level, copper layers in electronic devices.

The trend of portability combined with increased functionality of electronic devices has driven the miniaturization of PCBs. Conventional multilayer PCBs with through-hole interconnects are not always a practical solution. Alternative approaches for high density interconnects have been developed, such as sequential build up technologies, which utilize blind vias. One of the objectives in processes that use blind vias is the maximizing of via filling while minimizing thickness variation in the copper deposit between the vias and the substrate surface. This is particularly challenging when the PCB contains both through-holes and blind vias.

Leveling agents are used in copper plating baths to level the deposit across the substrate surface and to improve the throwing power of the electroplating bath. Throwing power is defined as the ratio of the through-hole center copper deposit thickness to its thickness at the surface. Newer PCBs are being manufactured that contain both through-holes and blind vias. Current bath additives, in particular current leveling agents, do not always provide level copper deposits between the substrate surface and filled through-holes and blind vias. Via fill is characterized by the difference in height between the copper in the filled via and the surface. Accordingly, there remains a need in the art for leveling agents for use in metal electroplating baths for the manufacture of PCBs that provide level copper deposits while bolstering the throwing power of the bath.

SUMMARY OF THE INVENTION

Compounds include reaction products of one or more amino acids and one more epoxies.

Compositions include one or more sources of copper ions, an electrolyte and one or more compounds of reaction products of one or more amino acids and one or more epoxies.

Methods include providing a substrate; providing a composition including one or more sources of copper ions, an electrolyte and one or more compounds of reaction products of one or more amino acids and one or more epoxies; and plating copper or copper alloy on the substrate.

The compounds provide copper or copper alloy layers having a substantially level and uniform surface across a substrate, even on substrates having small features and on substrates having a variety of feature sizes. The plating methods effectively deposit copper and copper alloys on substrates and in blind vias and through-holes such that the copper or copper alloy plating compositions have good throwing power. In addition, copper and copper alloy deposits have good physical reliability in response to thermal shock stress tests.

DETAILED DESCRIPTION OF THE INVENTION

As used throughout this specification the following abbreviations shall have the following meanings unless the context clearly indicates otherwise: A=amperes; $A/dm^2$=amperes per square decimeter; ft=foot; $A/ft^2$=amperes per foot squared; ° C.=degrees Centigrade; g=gram; ppm=parts per million=mg/L; L=liter, μm=micron=micrometer; mm=millimeters; cm=centimeters; DI=deionized; mL=milliliter; mol=moles; Mw=weight average molecular weight; and Mn=number average molecular weight. All numerical ranges are inclusive and combinable in any order, except where it is clear that such numerical ranges are constrained to add up to 100%.

As used throughout the specification, "feature" refers to the geometries on a substrate. "Aperture" refers to recessed features including through-holes and blind vias. As used throughout this specification, the term "plating" refers to metal electroplating. "Deposition" and "plating" are used interchangeably throughout this specification. "Leveler" refers to an organic compound or salt thereof that is capable of providing a substantially level or planar metal layer. The terms "leveler" and "leveling agent" are used interchangeably throughout this specification. "Accelerator" refers to an organic additive that increases the plating rate of the electroplating bath. "Suppressor" refers to an organic additive that suppresses the plating rate of a metal during electroplating. The terms "printed circuit boards" and "printed wiring boards" are used interchangeably throughout this specification. The term "moiety" means a part of a molecule or polymer that may include either whole functional groups or parts of functional groups as substructures. The terms "moiety" and "group" are used interchangeably throughout the specification. The "----" dashed line in chemical structures means an optional double bond. The articles "a" and "an" refer to the singular and the plural.

Compounds are reaction products of one or more amino acids and one or more epoxies. The reaction products may be used in copper and copper alloy electroplating compositions to plate copper or copper alloy deposits on substrates that may include blind vias, through-holes or combinations thereof. The copper and copper alloy electroplating compositions have good throwing power and the copper and copper alloy deposits have good physical reliability in response to thermal shock stress tests.

Amino acid monomers include both natural and synthetic amino acids and salts thereof, such as alkali metal salts. Amino acids include an amino group, a carboxyl group, a hydrogen atom and an amino acid side chain moiety all bonded, in the case of an α-amino acid, to a single carbon atom that is referred to as an α-carbon. The amino acids may also include β-amino acids and γ-amino acids.

α-Amino acid side chains include, but are not limited to, those disclosed in Table 1 below:

TABLE 1

| Amino Acid Structure | Amino Acid |
|---|---|
| H₂N—CHC(=O)—OH, side chain H | Glycine |
| H₂N—CHC(=O)—OH, side chain CH₃ | Alanine |
| H₂N—CHC(=O)—OH, side chain CH(CH₃)CH₃ | Valine |
| H₂N—CHC(=O)—OH, side chain CH₂CH(CH₃)CH₃ | Leucine |

TABLE 1-continued

| Amino Acid Structure | Amino Acid |
|---|---|
| H₂N—CHC(=O)—OH, side chain CH(CH₃)CH₂CH₃ | Isoleucine |
| H₂N—CHC(=O)—OH, side chain (CH₂)₄NH₂ | Lysine |
| H₂N—CHC(=O)—OH, side chain (CH₂)₃NH—C(=NH)NH₂ | Arginine |
| H₂N—CHC(=O)—OH, side chain CH₂-imidazole | Histidine |
| H₂N—CHC(=O)—OH, side chain CH₂—C(=O)—CH₂—C(=O)OH | Aspartic acid |
| H₂N—CHC(=O)—OH, side chain CH₂—C(=O)NH₂ | Asparagine |

TABLE 1-continued

| Amino Acid Structure | Amino Acid |
|---|---|
| $H_2N-CHC(=O)-OH$, side chain: $-CH_2-CH_2-C(=O)-NH_2$ | Glutamine |
| $H_2N-CHC(=O)-OH$, side chain: $-CH_2-C_6H_5$ | Phenylalanine |
| $H_2N-CHC(=O)-OH$, side chain: $-CH_2-C_6H_4-OH$ | Tyrosine |
| $H_2N-CHC(=O)-OH$, side chain: $-CH_2$-(indole) | Trytophan |
| $H_2N-CHC(=O)-OH$, side chain: $-CH_2-SH$ | Cysteine |
| $H_2N-CHC(=O)-OH$, side chain: $-CH_2-CH_2-S-CH_3$ | Methionine |
| $H_2N-CHC(=O)-OH$, side chain: $-CH_2-OH$ | Serine |

TABLE 1-continued

| Amino Acid Structure | Amino Acid |
|---|---|
| $H_2N-CHC(=O)-OH$, side chain: $-CH_2-CH_2-CH_2-NH_2$ | ornithine |
| $H_2N-CHC(=O)-OH$, side chain: $-CH(OH)-C_6H_5$ | 3-Phenylserine |
| $H_2N-CHC(=O)-OH$, side chain: $-CH(OH)-CH_3$ | Threonine |
| $H_2N-CHC(=O)-OH$, side chain: $-CH_2-C_6H_3(OH)_2$ | L-DOPA |
| $H_2N-CHC(=O)-OH$, side chain: $-CH_2-CH_2-CH_3$ | Norleucine |
| $H_2N-CHC(=O)-OH$, side chain: $-C(SH)(CH_3)-CH_3$ | Penicillamine |

α-Amino acids may also include sarcosine and heterocyclic amino acids such as proline, hydroxyproline, 3-hydroxyprolines, 3,4-dihydroproline and pipecolinic acid.

β-Amino acid side chains include, but are not limited to those in Table 2 below:

TABLE 2

| Amino Acid Structure | Amino Acid |
|---|---|
| $H_2N-CH_2-CH_2-C(=O)-OH$ | β-Alanine |
| $H_2N-CH(CH_3)-CH_2-C(=O)-OH$ | 3-Aminobutanoic Acid |
| $H_2N-CH_2-CH(OH)-C(=O)-OH$ | Isoserine |
| $H_2N-CH_2-CH(CH_3)-C(=O)-OH$ | 3-Aminoisobutyric acid |
| $H_2N-CH(C_6H_5)-CH_2-C(=O)-OH$ (with phenyl on α-C to NH$_2$) | 3-Amino-2-phenylpropionic acid |
| $H_2N-CH(CH_2CH(CH_3)_2)-CH_2-C(=O)-OH$ | 3-Amino-5-methylhexanoic acid |
| $H_2N-CH(CH_2C_6H_5)-CH_2-C(=O)-OH$ | 3-Amino-4-phenylbutyric acid |
| $H_2N-CH(CH_2OH)-CH_2-C(=O)-OH$ | 3-Amino-4-hydroxybutyric acid |
| $H_2N-CH(CH(OH)CH_3)-CH_2-C(=O)-OH$ | 3-Amino-4-hydroxypentanoic acid |
| $H_2N-CH(CH(CH_3)_2)-CH_2-C(=O)-OH$ | 3-Amino-4-methylpentanoic acid |

TABLE 2-continued

| Amino Acid Structure | Amino Acid |
|---|---|
| $H_2N-CH(C_6H_5)-CH_2-C(=O)-OH$ | 3-Amino-3-phenylpropionic acid |
| Pyrrolidine-3-carboxylic acid structure | Pyrrolidine-3-carboxylic acid |

γ-Amino acid side chains include, but are not limited to those in Table 3 below:

TABLE 3

| Amino Acid Structure | Amino Acid |
|---|---|
| $H_2N-CH_2-CH_2-CH_2-C(=O)-OH$ | γ-Aminobutyric Acid |
| $H_2N-CH_2-CH(OH)-CH_2-C(=O)-OH$ | 4-Amino-3-hydroxybutyric acid |
| pyrrolidin-2-yl-propionic acid structure | 3-pyrrolidin-2-yl-propionic acid |
| $H_2N$-cyclohexyl-$C(=O)-OH$ | 3-Aminocyclohexanecarboxylic acid |
| $H_2N-C(=NH)-NH-CH_2-CH_2-CH_2-C(=O)-OH$ | 4-Guanidinobutyric acid |

The amino acids may be D or L optical isomers or mixtures of D and L optical isomers.

Amino acids also include aromatic compounds having a general formula:

$$X'—COOH \quad (I)$$

where X' is a substituted six membered aromatic ring or a substituted aromatic six membered heterocyclic ring where the hetero-atom is nitrogen. Substituents groups include one or more of —NH$_2$ and —OH. Such compounds are shown in Table 4 below:

TABLE 4

| Amino Acid Structure | Amino Acid |
|---|---|
| | 4-Aminobenzoic acid |
| | 3-Aminobenzoic acid |
| | 2-Aminobenzoic acid |
| | 3,5-Diaminobenzoic acid |
| | 4-Aminosalicylic acid |
| | 5-Aminosalicyclic acid |
| | 3-Aminoisonicotinic acid |

TABLE 4-continued

| Amino Acid Structure | Amino Acid |
|---|---|
| | 4-Aminonicotinic acid |
| | 5-Aminonicotinic acid |
| | 2-Aminonicotinic acid |
| | 6-Aminonicotinic acid |
| | 2-Aminoisonicotinic acid |
| | 6-Aminopicolinic acid |

Preferably the aromatic amino acids are substituted six membered aromatic ring compounds.

Preferably the amino acids are the α-amino acids, the β-amino acids and the substituted six membered aromatic ring amino acids, more preferably, the amino acids are the α-amino acids and the substituted six membered aromatic ring amino acids. The preferred α-amino acids are the D or L isomers or mixtures thereof of arginine, glycine, alanine, tryptophan, lysine, histidine and tyrosine. The more preferred α-amino acids are the D or L isomers or mixtures thereof of arginine, glycine, alanine, lysine, histidine and tyrosine. The most preferred α-amino acids are the D or L isomers or mixtures thereof of arginine.

Optionally, in addition to one or more amino acids, one or more non-amino acid monomer amines may be included as a monomer in the reaction product. The amine may be acyclic or cyclic. Acyclic amines include, but are not limited to, primary, secondary or tertiary amines, linear or branched. Preferred amines are primary and secondary amines. Cyclic amines include, but are not limited to heterocyclic nitrogen compounds. The heterocyclic nitrogen compounds may be aromatic or non-aromatic. Heterocyclic nitrogen compounds include imidazoles, triazoles, tetrazoles, pyrazines, benzimidazoles, benzotriazoles, purines, piperazines, pyridazines, pyrazoles, triazines, tetrazines and pyrimidines.

The optional heterocyclic nitrogen compounds may have one or more substituent groups joined to the rings. Such substituent groups include linear or branched, substituted or unsubstituted alkyl, hydroxyl, nitro or nitroalkyl, nitroso or nitrosoalkyl, carbonyl, mercapto or mercaptoalkyl, linear or branched hydroxyalkyl, linear or branched alkoxy, substituted or unsubstituted aryl, linear or branched, substituted or unsubstituted arylalkyl, substituted or unsubstituted sulfonyl, linear or branched, substituted or unsubstituted amine. Substituent groups do not include carboxyl groups.

Heterocyclic nitrogen compounds may have the following general structure:

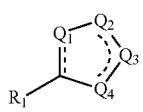

(II)

where $Q_1$-$Q_4$ may be nitrogen, oxygen, carbon, or sulfur with the proviso that at least one of the $Q_1$-$Q_4$ is nitrogen, and that only one of the $Q_1$-$Q_4$ may be oxygen or sulfur at any instance. When sulfur or oxygen is in the ring, sulfur or oxygen is at $Q_4$. Preferably, the ring has one to three nitrogen atoms, more preferably one or two nitrogen atoms. Most preferably, the ring is an imidazole. The carbon atoms and nitrogen atoms may be substituted or unsubstituted. Substituents on carbon atoms and nitrogen atoms, including $R_1$, include linear or branched, substituted or unsubstituted $(C_1$-$C_{10})$alkyl; hydroxyl; linear or branched alkoxy; linear or branched, substituted or unsubstituted hydroxy$(C_1$-$C_{10})$ alkyl; linear or branched, substituted or unsubstituted alkoxy $(C_1$-$C_{10})$alkyl; linear or branched, substituted or unsubstituted amino$(C_1$-$C_{10})$alkyl; substituted or unsubstituted aryl; linear or branched, substituted or unsubstituted aryl$(C_1$-$C_{10})$ alkyl; substituted or unsubstituted sulfonyl; and substituted or unsubstituted amine. Substituent groups do not include carboxyl groups. When $Q_1$ is carbon, $R_1$ and the substituent on $Q_1$ may be taken together with all of their atoms to form a six-membered carbon or heterocyclic aromatic fused ring with the ring of structure (II).

Heterocyclic nitrogen compounds where $R_1$ and the substituent on $Q_1$ when $Q_1$ is carbon are taken together to form a six-membered aromatic fused ring may have the following general structure:

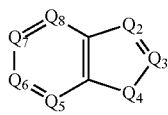

(III)

where $Q_2$-$Q_4$ are as defined above and $Q_5$-$Q_8$ may be carbon or nitrogen atoms with the proviso that only two of $Q_5$-$Q_8$ may be nitrogen at an instance. The carbon and nitrogen atoms for the rings may be substituted or unsubstituted. Substituents include hydroxyl; linear or branched alkoxy; linear or branched, substituted or unsubstituted hydroxy$(C_1$-$C_{10})$alkyl; linear or branched, substituted or unsubstituted alkoxy$(C_1$-$C_{10})$alkyl; linear or branched, substituted or unsubstituted aryl; linear or branched, substituted or unsubstituted aryl$(C_1$-$C_{10})$alkyl; substituted or unsubstituted sulfonyl; and substituted or unsubstituted amine. Substituent groups do not include carboxyl groups.

Heterocyclic nitrogen compounds also include those having a general structure:

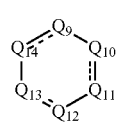

(IV)

where $Q_9$-$Q_{14}$ may be nitrogen, carbon or oxygen with the proviso that at least one of $Q_9$-$Q_{14}$ is nitrogen and there are no more than four nitrogen atoms in the ring. The carbon atoms and nitrogen atoms in the ring may be substituted or unsubstituted. Substituent groups may be the same or different and include those substituent groups described for $Q_1$-$Q_8$, above; however, substituent groups do not include carboxyl groups. When oxygen is present in the ring, only one of $Q_9$-$Q_{14}$ is oxygen at any instance. Heterocyclic nitrogen compounds of structure (IV) may be aromatic or non-aromatic heterocyclic nitrogen compounds.

Epoxide monomers include monomers having at least one epoxide group, preferably the epoxides are polyepoxides with 2-4 epoxide moieties. Such epoxides include, but are not limited to those having the following structures:

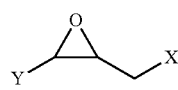

(V)

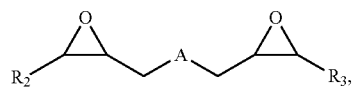

(VI)

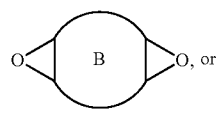

(VII)

(VIII)

where Y, $R_2$ and $R_3$ may be the same or different and are chosen from hydrogen and $(C_1$-$C_4)$alkyl, X is halogen, such as chlorine, bromine, fluorine and iodine, A=$OR_4$ or $R_5$;

$R_4=((CR_6R_7)_mO)$, (aryl-O)$_p$, $CR_6R_7$—Z—$CR_6CR_7$, or $OZ'_tO$, $R_5=(CH_2)_y$, B is $(C_5-C_{12})$cycloalkyl, Z=a 5- or 6-membered ring, Z' is $R_8OArOR_8$, $(R_9O)_bAr(OR_9)$, or $(R_9O)_b$, $Cy(OR_9)$, $Cy=(C_5-C_{12})$cycloalkyl; each $R_6$ and $R_7$ are independently chosen from hydrogen, methyl, or hydroxyl, each $R_8$ represents $(C_1-C_8)$alkyl, each $R_9$ represents a $(C_2-C_6)$alkyleneoxy; $R_{10}$ is a hydrogen atom, a formyl group, or one or two glycidyl ether groups each optionally containing a carbonyl group constituted by $C_4-C_8$ and $C_2-C_4$, $R_{11}$ is a hydrogen atom, a methyl group or an ethyl group, and $R_{12}$ is a hydrogen atom, a formyl group, or one or two glycidyl ether groups each optionally containing a carbonyl group constituted by $C_4-C_8$ and $C_2-C_4$, each b=1-10, m=1-6, n=1-4, p=1-6, t=1-4 and y=0-6. $R_2$ and $R_3$ are preferably independently chosen from hydrogen and $(C_1-C_2)$alkyl. When $R_2$ and $R_3$ are not joined to form a cyclic compound, it is preferred that $R_2$ and $R_3$ are both hydrogen. When $R_2$ and $R_3$ are joined to form a cyclic compound, it is preferred that A is $R_5$ or a chemical bond and that a $(C_8-C_{10})$carbocyclic ring is formed. It is preferred that m=2-4. Phenyl-O is the preferred aryl-O group for $R_4$. It is preferred that p=1-4, more preferably 1-3, and still more preferably 1-2. Z is preferably a 5- or 6-membered carbocyclic ring and, more preferably, Z is a 6-membered carbocyclic ring. Preferably, y=0-4, and more preferably, 1-4. When A=$R_5$ and y=0, then A is a chemical bond. Preferably, $Z'=R_8OArOR_8$ or $(R_9O)_bAr(OR_9)$. Each $R_8$ is preferably $(C_1-C_6)$alkyl and more preferably $(C_1-C_4)$alkyl. Each $R_9$ is preferably $(C_2-C_4)$alkyleneoxy. It is preferred that t=1-2. Preferably, b=1-8, more preferably, 1-6, and most preferably, 1-4. Each Ar group may be substituted with one or more substituent groups which include, but are not limited to, $(C_1-C_4)$alkyl, $(C_1-C_4)$alkoxy or halogen. Preferably Ar is $(C_6-C_{15})$aryl. Exemplary aryl groups are phenyl, methylphenyl, naphthyl, pyridinyl, bisphenylmethyl and 2,2-bisphenylpropyl. Preferably Cy is $(C_6-C_{15})$cycloalkyl. The $(C_5-C_{12})$cycloalkyl groups for B may be monocyclic, spirocyclic, fused or bicyclic groups. Preferably B is a $(C_8-C_{10})$cycloalkyl, more preferably, cyclooctyl. Preferably, $R_{10}$ and $R_{12}$ are independently a hydrogen atom or a glycidyl ether group and $R_{11}$ is a hydrogen atom or an ethyl group.

Compounds of formula (V) include, but are not limited to epichlorohydrin and epibromohydrin.

Compounds of formula (VI) include, but are not limited to, 1,4-butanediol diglycidyl ether, ethylene glycol diglycidyl ether, diethylene glycol diglycidyl ether, triethylene glycol diglycidyl ether, glycerol diglycidyl ether, neopentyl glycol diglycidyl ether, propylene glycol diglycidyl ether, dipropylene glycol diglycidyl ether and poly(propyleneglycol) diglycidyl ether.

Compounds of formula (VII) include, but are not limited to, dicyclopentadiene dioxide and 1,2,5,6-diepoxycyclooctane.

Compounds of formula (VIII) include, but are not limited to, glycerin triglycidyl ether, trimethylolpropanetriglycidyl ether, diglycerol tetraglycidyl ether, erythritol tetraglycidyl ether, arabinose tetraglycidyl ether, triglycerol pentaglycidyl ether, fructose pentaglycidyl ether, xylitol pentaglycidyl ether, tetraglycerol hexaglycidyl ether, and sorbitol hexaglycidyl ether.

The order of addition of monomers to a reaction vessel may vary, however, preferably, one or more amino acids are dissolved in water at 80° C. with dropwise addition of one or more epoxides. For reactants with poor water solubility small amounts of sulfuric acid or sodium hydroxide are added prior to epoxy addition. The temperature of the heating bath is then increased from 80° C. to 95° C. Heating with stirring is done for 2 hours to 4 hours. After an additional 6-12 hours of stirring at room temperature, the resulting reaction product is diluted with water. The reaction product may be used as-is in aqueous solution, may be purified or may be isolated as desired. Typically, the molar ratio of the amino acid compound to the epoxide-containing compound is from 0.1:10 to 10:0.1. Preferably, the molar ratio is from 1:5 to 5:1 and more preferably from 1:2 to 2:1. Other suitable ratios of amino acid compound to epoxide-containing compound may be used to prepare the present leveling agents. If one or more amines are included in addition to the amino acids and epoxides, amines are included in molar amounts of 100:1 to 1:100 to the amino acid, preferably from 20:1 to 1:20. Amines are typically added to the reaction vessel prior to adding the epoxides.

Preferably the reaction product consists of one or more amino acid monomers and one or more epoxide monomers, more preferably the reaction product consists of one or more amino acid monomers and one more polyepoxide monomers.

The plating compositions and methods which include one or more of the reaction products are useful in providing a substantially level and uniform plated metal layer on a substrate, such as a printed circuit board or semiconductor chip. Also, the plating compositions and methods are useful in filling apertures in a substrate with metal. The metal deposits have good throwing power and good physical reliability in response to thermal shock stress tests.

Any substrate upon which metal can be electroplated may be used as a substrate with the metal plating compositions containing the reaction products. Such substrates include, but are not limited to printed wiring boards, integrated circuits, semiconductor packages, lead frames and interconnects. An integrated circuit substrate may be a wafer used in a dual damascene manufacturing process. Such substrates typically contain a number of features, particularly apertures, having a variety of sizes. Through-holes in a PCB may have a variety of diameters, such as from 50 μm to 350 μm in diameter. Such through-holes may vary in depth, such as from 0.8 mm to 10 mm. PCBs may contain blind vias having a wide variety of sizes, such as up to 200 μm diameter and 150 μm depth, or greater.

Conventional copper and tin/copper alloy plating compositions may be used. The copper plating compositions contain a source of copper ions, an electrolyte, and a leveling agent, where the leveling agent is a reaction product of one or more amino acid monomers, one or more epoxide monomers and optionally one or more non-amino acid amine monomers. The copper plating compositions may contain a source of halide ions, an accelerator and a suppressor. Metals which may be electroplated from the compositions include copper and tin/copper alloys. Preferably the metal plated is copper.

Suitable copper ion sources are copper salts and include without limitation copper sulfate; copper halides such as copper chloride; copper acetate; copper nitrate; copper tetrafluoroborate; copper alkylsulfonates; copper aryl sulfonates; copper sulfamate; copper perchlorate and copper gluconate. Exemplary copper alkane sulfonates include copper $(C_1-C_6)$alkane sulfonate and more preferably copper $(C_1-C_3)$alkane sulfonate. Preferred copper alkane sulfonates are copper methanesulfonate, copper ethanesulfonate and copper propanesulfonate. Exemplary copper arylsulfonates include, without limitation, copper benzenesulfonate and copper p-toluenesulfonate. Mixtures of copper ion sources may be used. One or more salts of metal ions other than copper ions may be added to the present electroplating baths.

Typically, the copper salt is present in an amount sufficient to provide an amount of copper metal of 10 to 400 g/L of plating solution.

Suitable tin compounds include, but are not limited to salts, such as tin halides, tin sulfates, tin alkane sulfonate such as tin methane sulfonate, tin aryl sulfonate such as tin benzenesulfonate and tin p-toluenesulfonate. The amount of tin compound in these electrolyte compositions is typically an amount that provides a tin content in the range of 5 to 150 g/L. Mixtures of tin compounds may be used in an amount as described above.

The electrolyte useful in the present invention may be alkaline or acidic. Preferably the electrolyte is acidic. Preferably, the pH of the electrolyte is ≤2. Suitable acidic electrolytes include, but are not limited to, sulfuric acid, acetic acid, fluoroboric acid, alkanesulfonic acids such as methanesulfonic acid, ethanesulfonic acid, propanesulfonic acid and trifluoromethane sulfonic acid, aryl sulfonic acids such as benzenesulfonic acid, p-toluenesulfonic acid, sulfamic acid, hydrochloric acid, hydrobromic acid, perchloric acid, nitric acid, chromic acid and phosphoric acid. Mixtures of acids may be advantageously used in the present metal plating baths. Preferred acids include sulfuric acid, methanesulfonic acid, ethanesulfonic acid, propanesulfonic acid, hydrochloric acid and mixtures thereof. The acids may be present in an amount in the range of 1 to 400 g/L. Electrolytes are generally commercially available from a variety of sources and may be used without further purification.

Such electrolytes may optionally contain a source of halide ions. Typically chloride ions are used. Exemplary chloride ion sources include copper chloride, tin chloride, sodium chloride, potassium chloride and hydrochloric acid. A wide range of halide ion concentrations may be used in the present invention. Typically, the halide ion concentration is in the range of 0 to 100 ppm based on the plating bath. Such halide ion sources are generally commercially available and may be used without further purification.

The plating compositions typically contain an accelerator. Any accelerators (also referred to as brightening agents) are suitable for use in the present invention. Such accelerators are well-known to those skilled in the art. Accelerators include, but are not limited to, N,N-dimethyl-dithiocarbamic acid-(3-sulfopropyl)ester; 3-mercapto-propylsulfonic acid-(3-sulfopropyl)ester; 3-mercapto-propylsulfonic acid sodium salt; carbonic acid, dithio-O-ethylester-S-ester with 3-mercapto-1-propane sulfonic acid potassium salt; bis-sulfopropyl disulfide; bis-(sodium sulfopropyl)-disulfide; 3-(benzothiazolyl-S-thio)propyl sulfonic acid sodium salt; pyridinium propyl sulfobetaine; 1-sodium-3-mercaptopropane-1-sulfonate; N,N-dimethyl-dithiocarbamic acid-(3-sulfoethyl)ester; 3-mercapto-ethyl propylsulfonic acid-(3-sulfoethyl)ester; 3-mercapto-ethylsulfonic acid sodium salt; carbonic acid-dithio-O-ethylester-S-ester with 3-mercapto-1-ethane sulfonic acid potassium salt; bis-sulfoethyl disulfide; 3-(benzothiazolyl-S-thio)ethyl sulfonic acid sodium salt; pyridinium ethyl sulfobetaine; and 1-sodium-3-mercaptoethane-1-sulfonate. Accelerators may be used in a variety of amounts. In general, accelerators are used in an amount in a range of 0.1 ppm to 1000 ppm.

Any compound capable of suppressing the metal plating rate may be used as a suppressor in the present electroplating compositions. Suitable suppressors include, but are not limited to, polypropylene glycol copolymers and polyethylene glycol copolymers, including ethylene oxide-propylene oxide ("EO/PO") copolymers and butyl alcohol-ethylene oxide-propylene oxide copolymers. Suitable butyl alcohol-ethylene oxide-propylene oxide copolymers are those having a weight average molecular weight of 100 to 100,000, preferably 500 to 10,000. When such suppressors are used, they are typically present in an amount in the range of 1 to 10,000 ppm based on the weight of the composition, and more typically from 5 to 10,000 ppm. The leveling agents of the present invention may also possess functionality capable of acting as suppressors.

In general, the reaction products have a number average molecular weight (Mn) of 200 to 100,000, typically from 300 to 50,000, preferably from 500 to 30,000, although reaction products having other Mn values may be used. Such reaction products may have a weight average molecular weight (Mw) value in the range of 1000 to 50,000, typically from 5000 to 30,000, although other Mw values may be used.

The amount of the reaction product (leveling agent) used in the metal electroplating compositions depends upon the particular leveling agents selected, the concentration of the metal ions in the electroplating composition, the particular electrolyte used, the concentration of the electrolyte and the current density applied. In general, the total amount of the leveling agent in the electroplating composition ranges from 0.01 ppm to 500 ppm, preferably from 0.1 ppm to 250 ppm, most preferably from 0.5 ppm to 100 ppm, based on the total weight of the plating composition, although greater or lesser amounts may be used.

The electroplating compositions may be prepared by combining the components in any order. It is preferred that the inorganic components such as source of metal ions, water, electrolyte and optional halide ion source are first added to the bath vessel, followed by the organic components such as leveling agent, accelerator, suppressor, and any other organic component.

The electroplating compositions may optionally contain at least one additional leveling agent. Such additional leveling agents may be another leveling agent of the present invention, or alternatively, may be any conventional leveling agent. Suitable conventional leveling agents that can be used in combination with the present leveling agents include, without limitations, those disclosed in U.S. Pat. No. 6,610,192 to Step et al., U.S. Pat. No. 7,128,822 to Wang et al., U.S. Pat. No. 7,374,652 to Hayashi et al. and U.S. Pat. No. 6,800,188 to Hagiwara et al. Such combination of leveling agents may be used to tailor the characteristics of the plating bath, including leveling ability and throwing power.

Typically, the plating compositions may be used at any temperature from 10 to 65° C. or higher. Preferably, the temperature of the plating composition is from 10 to 35° C. and more preferably from 15 to 30° C.

In general, the metal electroplating compositions are agitated during use. Any suitable agitation method may be used and such methods are well-known in the art. Suitable agitation methods include, but are not limited to: air sparging, work piece agitation, and impingement.

Typically, a substrate is electroplated by contacting the substrate with the plating composition. The substrate typically functions as the cathode. The plating composition contains an anode, which may be soluble or insoluble. Potential is typically applied to the electrodes. Sufficient current density is applied and plating performed for a period of time sufficient to deposit a metal layer having a desired thickness on the substrate as well as to fill blind vias, trenches and through-holes, or to conformally plate through-holes. Current densities may range from 0.05 to 10 A/dm$^2$, although higher and lower current densities may be used. The specific current density depends in part upon the substrate to be plated, the composition of the plating bath, and the desired surface metal thickness. Such current density choice is within the abilities of those skilled in the art.

An advantage of the present invention is that substantially level metal deposits are obtained on a PCB. Through-holes, blind vias or combinations thereof in the PCB are substantially filled or through-holes are conformally plated with desirable throwing power. A further advantage of the present invention is that a wide range of apertures and aperture sizes may be filled or conformally plated with desirable throwing power.

Throwing power is defined as the ratio of the average thickness of the metal plated in the center of a through-hole compared to the average thickness of the metal plated at the surface of the PCB sample and is reported as a percentage. The higher the throwing power, the better the plating composition is able to conformally plate the through-hole. Metal plating compositions of the present invention may have a throwing power of ≥65%, preferably ≥70%.

The compounds provide metal layers having a substantially level surface across a substrate, even on substrates having small features and on substrates having a variety of feature sizes. The plating methods effectively deposit metals in through-holes such that the metal plating compositions have good throwing power.

While the methods of the present invention have been generally described with reference to printed circuit board manufacture, it is appreciated that the present invention may be useful in any electrolytic process where an essentially level or planar metal deposit and filled or conformally plated apertures are desired. Such processes include semiconductor packaging and interconnect manufacture.

The following examples are intended to further illustrate the invention but are not intended to limit its scope.

EXAMPLE 1

In 250 mL round-bottom, three-neck flask equipped with a condenser and a thermometer, 100 mmol of L-Arginine and 20 mL of deionized ("DI") water were added followed by addition of 100 mmol of 1,4-butanediol diglycidyl ether at 80° C. The resulting mixture was heated for about 5 hours using an oil bath set to 95° C. and then left to stir at room temperature for additional 6 hours. An amber-red colored viscous reaction product was transferred into a container, rinsed and adjusted with DI water. The reaction product solution was used without further purification.

Nine additional reaction products were prepared substantially according to the method described above except that the monomers were varied as disclosed in Table 5.

TABLE 5

| Reaction Product | Monomer 1 ($M_1$) | Monomer 2 ($M_2$) | Molar Ratio $M_1:M_2$ |
|---|---|---|---|
| 1 | H₂N—CHC(=O)—OH, CH₂, CH₂, CH₂, NH, C=NH, NH₂ (L-Arginine) | 1,4-Butanediol diglycidyl ether | 1:1 |
| 2 | H₂N—CHC(=O)—OH, CH₂, CH₂, CH₂, NH, C=NH, NH₂ | 1,2,7,8-Diepoxyoctane | 1:1 |
| 3 | H₂N—CHC(=O)—OH, CH₂, CH₂, CH₂, NH, C=NH, NH₂ | Poly(ethylene glycol)diglycidyl ether, Mw = 526 | 1:1 |
| 4 | H₂N—CHC(=O)—OH, CH₂, CH₂, CH₂, NH, C=NH, NH₂ | Neopentyl glycol diglycidyl ether | 1:1 |
| 5 | H₂N—CHC(=O)—OH, CH₂, CH₂, CH₂, NH, C=NH, NH₂ | Glycerol diglycidyl ether | 1:1 |

TABLE 5-continued

| Reaction Product | Monomer 1 ($M_1$) | Monomer 2 ($M_2$) | Molar Ratio $M_1:M_2$ |
|---|---|---|---|
| 6 | H$_2$N—CHC(=O)—OH with side chain —CH$_2$—CH$_2$—CH$_2$—NH—C(=NH)—NH$_2$ | 1,2,5,6-diepoxyhexane | 1:1 |
| 7 | H$_2$N—CHC(=O)—OH with side chain —CH$_2$—CH$_2$—CH$_2$—NH—C(=NH)—NH$_2$ | Poly(propylene glycol) diglycidyl ether, Mn = 380 | 1:1 |
| 8 | H$_2$N—CHC(=O)—OH with side chain —CH$_2$—CH$_2$—CH$_2$—NH—C(=NH)—NH$_2$ | Poly(propylene glycol) diglycidyl ether, Mw = 640 | 1:1 |
| 9 | H$_2$N—CHC(=O)—OH with side chain —CH$_2$—CH$_2$—CH$_2$—NH—C(=NH)—NH$_2$ | Epichlorohydrin | 1:1 |
| 10 | H$_2$N—CHC(=O)—OH with side chain —CH$_2$—CH$_2$—CH$_2$—NH—C(=NH)—NH$_2$ | 1,2,5,6-Diepxycyclooctane | 1:1 |

EXAMPLE 2

L-Arginine (75 mmol) and 25 mmol of 3-aminobenzoic acid were added at room temperature into a round-bottom reaction flask. Then, 20 mL of DI water was added to the mixture. The solution was heated to 85° C. Then 1,4-Butanediol diglycidyl ether (100 mmol) was added dropwise using addition funnel. The reaction mixture was heated for additional 4 hours using an oil bath set to 95° C. and left stirring at room temperature for another 8 hours. The resulting amber colored reaction product was transferred into a storage container, rinsed and diluted with water. The reaction product solution was used without further purification.

Eight additional reaction products were prepared substantially according to the method described above except that the monomers were varied as disclosed in Table 6.

TABLE 6

| Reaction Product | Monomer 1 ($M_1$) | Monomer 2 ($M_2$) | Monomer 3 ($M_3$) | Molar Ratio $M_1:M_2:M_3$ |
|---|---|---|---|---|
| 11 | H$_2$N—CHC(=O)—OH with side chain —CH$_2$—CH$_2$—CH$_2$—NH—C(=NH)—NH$_2$ | 3-aminobenzoic acid (COOH, NH$_2$ on benzene) | glycidyl ether: epoxide—CH$_2$—O—(CH$_2$)$_4$—O—CH$_2$—epoxide | 3:1:4 |

TABLE 6-continued

| Reaction Product | Monomer 1 (M₁) | Monomer 2 (M₂) | Monomer 3 (M₃) | Molar Ratio $M_1:M_2:M_3$ |
|---|---|---|---|---|
| 12 | Arginine (H₂N—CHC(=O)—OH with side chain —CH₂—CH₂—CH₂—NH—C(=NH)—NH₂) | 3-aminobenzoic acid (COOH, NH₂ on benzene) | Glycidyl ether (epoxy-CH₂—O—(CH₂)₄—O—CH₂-epoxy) | 1:1:2 |
| 13 | Arginine | 3-aminobenzoic acid | Glycidyl ether (as above) | 1:3:4 |
| 14 | Arginine | 4-phenyl-1H-imidazole | Glycidyl ether (as above) | 3:1:4 |
| 15 | Arginine | 4-phenyl-1H-imidazole | Glycidyl ether (as above) | 1:1:2 |

TABLE 6-continued

| Reaction Product | Monomer 1 (M₁) | Monomer 2 (M₂) | Monomer 3 (M₃) | Molar Ratio M₁:M₂:M₃ |
|---|---|---|---|---|
| 16 | Arginine | 4-phenylimidazole | 1,4-butanediol diglycidyl ether | 1:3:4 |
| 17 | Arginine | Glycine | 1,4-butanediol diglycidyl ether | 1:1:2 |
| 18 | Arginine | Resorcinol diglycidyl ether | 1,4-butanediol diglycidyl ether | 10:1:9 |
| 19 | Arginine | 1,4-cyclohexanedimethanol diglycidyl ether | 1,4-butanediol diglycidyl ether | 10:1:9 |

EXAMPLE 3

A plurality of copper electroplating baths were prepared by combining 75 g/L copper as copper sulfate pentahydrate, 240 g/L sulfuric acid, 60 ppm chloride ion, 1-2 ppm of an accelerator and 1.5 g/L of a suppressor. The accelerator was bis(sodium-sulfopropyl)disulfide. The suppressor was an EO/PO copolymer having a weight average molecular weight of <5,000 and terminal hydroxyl groups. Each electroplating bath also contained one of the reaction products from Examples 1 or 2 in amounts of 0.1 to 100 ppm as shown in Table 7, in Example 4 below. The reaction products were used without purification.

EXAMPLE 4

Samples of a 1.6 mm thick of double-sided FR4 PCBs, 5 cm×9.5 cm, having a plurality of through-holes were electroplated with copper in Haring cells using the copper electroplating baths of Example 3. The 1.6 mm thick samples had 0.25 mm diameter through-holes. The temperature of each bath was 25° C. A current density of 3.24 A/dm$^2$ (30 A/ft$^2$) was applied to the 1.6 mm samples for 44 minutes. The copper plated samples were sectioned and at least 10 holes per sample were analyzed to determine the throwing power ("TP") of the plating bath, and percent cracking according to the following methods.

Throwing power was calculated by determining the ratio of the average thickness of the metal plated in the center of a through-hole compared to the average thickness of the metal plated at the surface of the PCB sample. The throwing power is reported in Table 7 as a percentage.

The percent cracking was determined according to the industry standard procedure, IPC-TM-650-2.6.8. Thermal Stress, Plated-Through Holes, published by IPC (Northbrook, Ill., USA), dated May, 2004, revision E.

TABLE 7

| Reaction Product | Leveler Amount, ppm | Accelerator Amount, ppm | % Cracking | % TP |
|---|---|---|---|---|
| 7 | 1 | 1 | 0 | 83 |
|   | 5 | 1 | 0 | 76 |
|   | 10 | 1 | 0 | 77 |
|   | 1 | 2 | 0 | 83 |
|   | 5 | 2 | 0 | 80 |
|   | 10 | 2 | 0 | 76 |
| 2 | 1 | 1 | 0 | 83 |
|   | 5 | 1 | 0 | 79 |
|   | 10 | 1 | 0 | 77 |
|   | 1 | 2 | 0 | 82 |
|   | 5 | 2 | 0 | 79 |
|   | 10 | 2 | 0 | 86 |
| 4 | 1 | 1 | 0 | 79 |
|   | 10 | 1 | 0 | 77 |
|   | 20 | 1 | 0 | 82 |
|   | 5 | 2 | 0 | 81 |
|   | 10 | 2 | 0 | 80 |
| 5 | 1 | 1 | 100 | 81 |
|   | 0.5 | 2 | 100 | 80 |
|   | 1 | 2 | 100 | 75 |
|   | 2 | 2 | 100 | 71 |
| 3 | 1 | 1 | 0 | 81 |
|   | 5 | 1 | 0 | 81 |
|   | 10 | 1 | 0 | 79 |
|   | 20 | 1 | 0 | 83 |
|   | 5 | 2 | 0 | 80 |
|   | 10 | 2 | 0 | 81 |
|   | 20 | 2 | 0 | 82 |
| 19 | 1 | 1 | 0 | 82 |
|   | 5 | 1 | 0 | 83 |

TABLE 7-continued

| Reaction Product | Leveler Amount, ppm | Accelerator Amount, ppm | % Cracking | % TP |
|---|---|---|---|---|
|   | 1 | 2 | 0 | 81 |
|   | 5 | 2 | 0 | 85 |
|   | 10 | 2 | 0 | 80 |
| 8 | 1 | 1 | 0 | 92 |
|   | 5 | 1 | 0 | 82 |
|   | 20 | 1 | 0 | 86 |
|   | 1 | 2 | 0 | 84 |
|   | 5 | 2 | 0 | 89 |
|   | 10 | 2 | 0 | 82 |
| 18 | 1 | 1 | 0 | 83 |
|   | 5 | 1 | 0 | 76 |
|   | 1 | 2 | 0 | 79 |
|   | 5 | 2 | 0 | 77 |
| 6 | 1 | 1 | 0 | 77 |
|   | 5 | 1 | 0 | 71 |
|   | 10 | 1 | 0 | 76 |
|   | 5 | 2 | 0 | 74 |
|   | 10 | 2 | 0 | 71 |
| 9 | 1 | 1 | 0 | 87 |
|   | 5 | 1 | 0 | 90 |
|   | 10 | 1 | 0 | 85 |
|   | 20 | 1 | 0 | 88 |
|   | 10 | 2 | 0 | 75 |
| 10 | 5 | 1 | 0 | 71 |
|   | 10 | 1 | 0 | 80 |
|   | 20 | 1 | 0 | 78 |
| 11 | 0.25 | 1 | 0 | 85 |
|   | 0.5 | 1 | 0 | 83 |
|   | 1 | 1 | 0 | 86 |
|   | 5 | 1 | 0 | 79 |
|   | 10 | 1 | 0 | 82 |
|   | 20 | 1 | 0 | 80 |
| 12 | 0.1 | 1 | 10 | 85 |
|   | 0.25 | 1 | 40 | 79 |
|   | 0.1 | 2 | 5 | 81 |
|   | 0.25 | 2 | 0 | 80 |
| 13 | 0.1 | 1 | 0 | 78 |
|   | 0.25 | 1 | 33 | 92 |
|   | 0.1 | 2 | 0 | 74 |
|   | 0.25 | 2 | 0 | 94 |
| 14 | 1 | 1 | 0 | 81 |
|   | 5 | 1 | 0 | 83 |
|   | 10 | 1 | 0 | 86 |
|   | 20 | 1 | 0 | 82 |
| 15 | 0.25 | 1 | 0 | 82 |
|   | 0.5 | 1 | 0 | 85 |
|   | 1 | 1 | 0 | 82 |
|   | 5 | 1 | 0 | 77 |
| 16 | 1 | 1 | 0 | 89 |
|   | 5 | 1 | 0 | 77 |
|   | 10 | 1 | 0 | 79 |
|   | 20 | 1 | 0 | 78 |
| 17 | 1 | 1 | 0 | 84 |
|   | 5 | 1 | 0 | 82 |
|   | 10 | 1 | 0 | 84 |
|   | 20 | 1 | 0 | 81 |

The majority of the results showed that the throwing power exceeded 70%, indicating superior throwing power performance for the reaction products. Although major cracking was observed in reaction product 5, the majority of samples observed showed significant reduction in cracking. The lower the percentage of cracking, the better was the plating performance. Preferably, cracking is ≤10%.

EXAMPLE 5

The method described in Example 4 above was repeated except that the samples were 3.2 mm thick double-sided FR4 PCBs with 0.3 mm diameter through-holes plated at a current density of 2.16 A/dm$^2$ (20 A/ft$^2$). The cracking and TP results are shown below in Table 8.

TABLE 8

| Reaction Product | Leveler Amount, ppm | % Cracking | % TP |
|---|---|---|---|
| 7 | 1 | 0 | 75 |
|   | 2 | 0 | 75 |
|   | 5 | 0 | 77 |
| 2 | 1 | 0 | 74 |
|   | 10 | 0 | 70 |
| 4 | 5 | 0 | 78 |
|   | 20 | 0 | 79 |
| 5 | 0.25 | 23 | 78 |
|   | 1 | 100 | 72 |
| 3 | 10 | 0 | 74 |
|   | 20 | 0 | 69 |
| 19 | 1 | 0 | 71 |
|   | 5 | 0 | 70 |
|   | 10 | 0 | 69 |
| 8 | 1 | 0 | 67 |
|   | 2 | 0 | 71 |
|   | 5 | 3 | 73 |
| 18 | 1 | 0 | 72 |
|   | 10 | 0 | 67 |
| 6 | 1 | 0 | 47 |
|   | 5 | 0 | 50 |
|   | 10 | 0 | 49 |
| 9 | 1 | 0 | 48 |
|   | 5 | 0 | 54 |
|   | 10 | 0 | 53 |
| 10 | 5 | 0 | 47 |
|   | 10 | 0 | 48 |
|   | 20 | 0 | 49 |
| 11 | 1 | 0 | 67 |
|   | 2 | 0 | 68 |
|   | 5 | 0 | 66 |
| 12 | 0.25 | 0 | 71 |
|   | 0.5 | 0 | 73 |
| 13 | 0.5 | 0 | 82 |
|   | 1 | 0 | 82 |
|   | 2 | 0 | 94 |
| 14 | 1 | 0 | 66 |
|   | 5 | 0 | 70 |
|   | 10 | 0 | 71 |
| 15 | 0.25 | 0 | 63 |
|   | 0.5 | 0 | 72 |
|   | 1 | 0 | 77 |
| 16 | 0.25 | 0 | 68 |
|   | 0.5 | 0 | 72 |
|   | 1 | 12 | 77 |
| 17 | 1 | 0 | 62 |
|   | 5 | 0 | 70 |
|   | 10 | 0 | 71 |

With the exception of two samples from reaction product 5, reduction in cracking was significant. Overall % TP was good except for reaction products 6, 9, 10 and 11.

EXAMPLE 6 (COMPARATIVE)

Two copper electroplating baths were prepared by combining 75 g/L copper as copper sulfate pentahydrate, 240 g/L sulfuric acid, 60 ppm chloride ion, 1 ppm of an accelerator and 1.5 g/L of a suppressor. The accelerator was bis(sodium-sulfopropyl)disulfide. The suppressor was an EO/PO copolymer having a weight average molecular weight of <5,000 and terminal hydroxyl groups. One of the two baths was used to conformally plate 0.25 mm diameter through-holes in a 1.6 mm thick double-sided FR4 PCB, 5 cm×9.5 cm, for 44 minutes at a current density of 3.24 A/dm$^2$ (30 A/ft$^2$) and the second bath was used to plate 0.3 mm diameter through-holes in a 3.2 mm thick double-sided FR4 PCB of 80 minutes at a current density of 2.16 A/dm$^2$ (20 A/ft$^2$). Copper electroplating was done in Haring cells. The temperature of each bath was 25° C. The copper plated samples were analyzed to determine the throwing power ("TP") of the plating bath, and percent cracking. At least 10 samples from each board were analyzed. The results are shown in Table 10 below.

TABLE 10

| Board Thickness, mm | % Cracking | % TP |
|---|---|---|
| 1.6 | 0 | 69 |
| 3.2 | 0 | 43 |

Although no cracking was observed in any of the plated samples, the average TP for each sample was below the target value of 70% or greater. Accordingly, the TP for the copper plating baths which excluded levelers was substandard and unacceptable from a commercial perspective.

EXAMPLE 7 (COMPARATIVE)

To a 100 mL round-bottom, three-neck flask equipped with condenser, thermometer, and stir bar 4.195 g (33 mmol) of trans-3-(3-pyridyl) acrylic acid and 3.055 g (33 mmol) of Epichlorohydrine were added. The mixture was diluted with 70 ml of DI water and heated under reflux for 2 hours. After that the heat was removed and the product was diluted with additional 30 ml of DI water and allowed to stir for another 8 hours. The molar ratio of acrylic acid moiety to epoxide moiety was 1:1 based on monomer molar ratios.

TABLE 11

| Comparative Reaction Product | Monomer 1 ($M_1$) | Monomer 2 ($M_2$) | $M_1:M_2$ |
|---|---|---|---|
| 1 | COOH group attached to vinyl-pyridine | Epichlorohydrin (epoxide-CH2-Cl) | 1:1 |

EXAMPLE 8 (COMPARATIVE)

A plurality of copper electroplating baths were prepared by combining 75 g/L copper as copper sulfate pentahydrate, 240 g/L sulfuric acid, 60 ppm chloride ion, 1 ppm of an accelerator and 1.5 g/L of a suppressor. The accelerator was bis(sodium-sulfopropyl)disulfide. The suppressor was an EO/PO copolymer having a weight average molecular weight of <5,000 and terminal hydroxyl groups. Each electroplating bath also contained the reaction product from Example 7 in amounts of 1 to 50 ppm as shown in Table 12. The reaction product was used without purification.

Samples of a 1.6 mm thick of double-sided FR4 PCBs, 5 cm×9.5 cm, having a plurality of through-holes were electroplated with copper in Haring cells using the copper electroplating baths. The 1.6 mm thick samples had 0.25 mm diameter through-holes. The temperature of each bath was 25° C. A current density of 3.24 A/dm$^2$ was applied to the 1.6 mm samples for 44 minutes. The copper plated samples were sectioned and were analyzed to determine the throwing power ("TP") of the plating bath, and percent cracking. At least 10 samples were analyzed for % cracking and % TP. The results are shown in Table 12.

TABLE 12

| Leveler Amount, ppm | % Cracking | % TP |
|---|---|---|
| 1 | 0 | 64 |
| 5 | 0 | 61 |

TABLE 12-continued

| Leveler Amount, ppm | % Cracking | % TP |
|---|---|---|
| 10 | 0 | 63 |
| 20 | 0 | 66 |
| 20 | 0 | 66 |
| 50 | 0 | 71 |

Although no cracking was observed in any of the plated samples, the average TP for each sample was below the target value of 70% or greater. Accordingly, the TP for the copper plating baths which included the reaction product of Example 7 was substandard and unacceptable from a commercial perspective.

EXAMPLE 9 (COMPARATIVE)

The method of Example 8 was repeated except that a current density of 2.16 A/dm$^2$ was applied to the 3.2 mm thick double-sided FR4 PCBs with a plurality of 0.3 mm diameter through-holes for 80 minutes. The leveler concentration was 20 ppm or 50 ppm. The results are shown in Table 13 below.

TABLE 13

| Leveler Amount, ppm | % Cracking | % TP |
|---|---|---|
| 20 | 0 | 48 |
| 50 | 0 | 54 |

As in Example 8, no cracking was observed; however, the TP was still substandard and unacceptable for commercial purposes.

EXAMPLE 10 (COMPARATIVE)

Trans-3-(3-pyridyl) acrylic acid (73 mmol) was added at room temperature into a round-bottom reaction flask. Then, 20 mL of DI water was added to the mixture. The solution was heated to 85° C. The formed suspension disappeared after addition of small amount of sulfuric acid. Then 1,4-Butanediol diglycidyl ether (73 mmol) was added dropwise using an addition funnel. The reaction mixture was heated for additional 6 hours using an oil bath set to 95° C. and left stirring at room temperature for another 8 hours. The resulting amber colored reaction product was transferred into a storage container, rinsed and diluted with acidified water. The reaction product solution was used without further purification. The molar ratio of acrylic acid moiety to epoxide moiety was 1:1 based on monomer molar ratios.

TABLE 14

| Comparative Reaction Product | Monomer 1 (M$_1$) | Monomer 2 (M$_2$) | M$_1$:M$_2$ |
|---|---|---|---|
| 2 | Trans-3-(3-pyridyl) acrylic acid (COOH-CH=CH-pyridyl) | 1,4-Butanediol diglycidyl ether | 1:1 |

EXAMPLE 11 (COMPARATIVE)

A plurality of copper electroplating baths were prepared by combining 75 g/L copper as copper sulfate pentahydrate, 240 g/L sulfuric acid, 60 ppm chloride ion, 1 ppm of an accelerator and 1.5 g/L of a suppressor. The accelerator was bis(sodium-sulfopropyl)disulfide. The suppressor was an EO/PO copolymer having a weight average molecular weight of <5,000 and terminal hydroxyl groups. Each electroplating bath also contained the reaction product from Example 10 in amounts from 1-50 ppm as shown in Table 15. The reaction product was used without purification.

Samples of a 1.6 mm thick of double-sided FR4 PCBs, 5 cm×9.5 cm, having a plurality of through-holes were electroplated with copper in Haring cells using the copper electroplating baths. The 1.6 mm thick samples had 0.25 mm diameter through-holes. The temperature of each bath was 25° C. A current density of 3.24 A/dm$^2$ was applied to the 1.6 mm samples for 44 minutes. The copper plated samples were sectioned and were analyzed to determine the throwing power ("TP") of the plating bath, and percent cracking. At least 10 samples were analyzed. The results are shown in Table 15.

TABLE 15

| Leveler Amount, ppm | % Cracking | % TP |
|---|---|---|
| 1 | 0 | 74 |
| 5 | 0 | 64 |
| 10 | 0 | 59 |
| 20 | 0 | 58 |
| 20 | 0 | 58 |
| 50 | 0 | 66 |

No cracking was observed. Although one sample had a % TP of 74, the remainder of the samples was below 70% thus substandard.

EXAMPLE 12 (COMPARATIVE)

The method of Example 11 was repeated except that a current density of 2.16 A/dm2 was applied to the 3.2 mm thick double-sided FR4 PCBs with a plurality of 0.3 mm diameter through-holes for 80 minutes. The leveler concentration was 20 ppm or 50 ppm. The results are shown in Table 16 below.

TABLE 16

| Leveler Amount, ppm | % Cracking | % TP |
|---|---|---|
| 20 | 0 | 39 |
| 50 | 0 | 41 |

As in Example 11, no cracking was observed; however, the % TP was substandard and unacceptable for commercial purposes.

What is claimed is:

1. A method comprising:
   a) providing a substrate;
   b) providing a composition comprising one or more sources of copper ions, an electrolyte, and one or more compounds consisting of a reaction product of one or more amino acid monomers and one or more polyepoxide monomers and optionally one or more heterocyclic nitrogen compound monomers;
   c) contacting the substrate with the composition;
   d) applying a current to the substrate and the composition; and
   e) depositing copper or copper alloy on the substrate.

2. The method of claim 1, wherein the one or more amino acids are chosen from α-amino acids, β-amino acids and γ-amino acids.

3. The method of claim 2, wherein the one or more α-amino acids are chosen from arginine, alanine, glycine, tryptophan, asparagine, lysine, histidine, tyrosine, glutamine, proline and salts thereof.

4. The method of claim 1, wherein a molar ratio of a moiety from the amino acid monomer to a moiety from the polyepoxide monomer ranges from 0.5:2-2:0.5.

5. The method of claim 1, wherein the one or more polyepoxide monomers have a formula:

(VI)

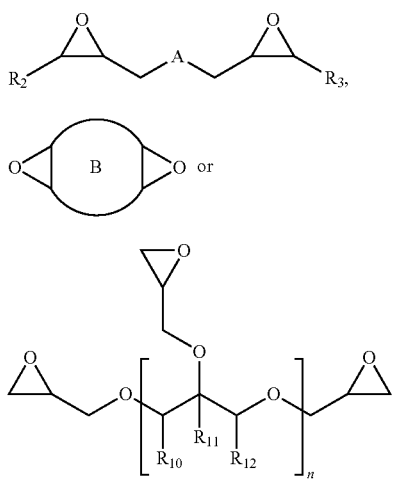

wherein $R_2$ and $R_3$ may be the same or different and are chosen from hydrogen and $(C_1-C_4)$alkyl, A =$OR_4$ or $R_5$; $R_4$=$((CR_6R_7)_mO)$, $(aryl-O)_p$, $CR_6R_7$—Z —$CR_6CR_7$, or $OZ'_tO$, $R_5$=$(CH_2)_y$, B is $(C_5-C_{12})$cycloalkyl, Z=a 5- or 6-membered ring, Z' is $R_8OArOR_8$, $(R_9O)_bAr(OR_9)$, or $(R_9O)_b$, $Cy(OR_9)$, Cy =$(C_5-C_{12})$cycloalkyl, $R_6$ and $R_7$ are independently chosen from hydrogen, methyl, or hydroxyl, $R_8$ represents $(C_1-C_8)$alkyl, $R_9$ represents a $(C_2-C_6)$alkyleneoxy, $R_{10}$ is a hydrogen atom, a formyl group, or one or two glycidyl ether groups each optionally containing a carbonyl group constituted by $C_4-C_8$ and $C_2-C_4$, $R_{11}$ is a hydrogen atom, a methyl group or an ethyl group, and $R_{12}$ is a hydrogen atom, a formyl group, or one or two glycidyl ether groups each optionally containing a carbonyl group constituted by $C_4-C_8$ and $C_2-C_4$, b=1-10, m=1-6, n=1-4, p=1-6, t=1-4 and y=0-6.

6. The method of claim 1 wherein the substrate comprises a plurality of one or more of through-holes, trenches and vias.

7. The method of claim 1, wherein the one or more polyepoxide monomers are chosen from 1,4-butanediol diglycidyl ether, ethylene glycol diglycidyl ether, diethylene glycol diglycidyl ether, triethylene glycol diglycidyl ether, glycerol diglycidyl ether, neopentyl glycol diglycidyl ether, propylene glycol diglycidyl ether, dipropylene glycol diglycidyl ether, poly(ethyleneglycol) diglycidyl ether and poly(propyleneglycol) diglycidyl ether.

8. The method of claim 1, wherein the one or more polyepoxide monomers are chosen from dicyclopentadiene dioxide and 1,2,5,6-diepoxycyclooctane.

9. The method of claim 1, wherein the one or more polyepoxide monomers are chosen from glycerin triglycidyl ether, trimethylolpropanetriglycidyl ether, diglycerol tetraglycidyl ether, erythritol tetraglycidyl ether, arabinose tetraglycidyl ether, triglycerol pentaglycidyl ether, fructose pentaglycidyl ether, xylitol pentaglycidyl ether, tetraglycerol hexaglycidyl ether, and sorbitol hexaglycidyl ether.

10. The method of claim 1, wherein the one or more amino acid monomers are chosen from aromatic compounds having a general formula:

$$X'—COOH \qquad (I)$$

wherein X' is a substituted six membered aromatic ring or a substituted six membered heterocyclic ring wherein the hetero-atom is nitrogen, and substituent groups are —$NH_2$ and optionally —OH.

11. The method of claim 10, wherein the one or more amino acid monomers is chosen from 4-aminobenzoic acid, 3-aminobenzoic acid, 2-aminobenzoic acid, 3,5-diaminobenzoic acid, 4-aminosalicylic acid and 5-aminosalicylic acid.

12. The method of claim 10, wherein the one or more amino acid monomers are chosen from 3-aminoisonicotinic acid, 4-aminonicotinic acid, 5-aminonicotinic acid, 2-aminonicotinic acid, 6-aminonicotinic acid, 2-aminoisonicotinic acid and 6-aminopicolinic acid.

13. The method of claim 1, wherein the one or more heterocyclic nitrogen compound monomers are chosen from imidazoles, triazoles, tetrazoles, pyrazines, benzimidazoles, benzotriazoles, purines, piperazines, pyridazines, pyrazoles, triazines, tetrazines and pyrimidines.

14. The method of claim 1, wherein the composition further comprises one or more sources of tin ions.

15. The method of claim 1, wherein the electrolyte is acidic.

16. The method of claim 15, wherein a pH of the electrolyte is <2.

* * * * *